US007300330B2

(12) United States Patent
Estrella Garrido

(10) Patent No.: US 7,300,330 B2
(45) Date of Patent: Nov. 27, 2007

(54) PROTECTION DISKS FOR BREASTFEEDING MOTHERS

(75) Inventor: Arsenia Estrella Garrido, Reus (ES)

(73) Assignee: Obee Innova S.L., Esponceda (ES)

( * ) Notice: Subject to any disclaimer, the term of this patent is extended or adjusted under 35 U.S.C. 154(b) by 0 days.

(21) Appl. No.: 10/537,773

(22) PCT Filed: Dec. 15, 2003

(86) PCT No.: PCT/EP03/14249

§ 371 (c)(1),
(2), (4) Date: Jun. 6, 2005

(87) PCT Pub. No.: WO2004/054495

PCT Pub. Date: Jul. 1, 2004

(65) Prior Publication Data

US 2006/0025040 A1 Feb. 2, 2006

(30) Foreign Application Priority Data

Dec. 18, 2002 (ES) ........................... 200203033 U

(51) Int. Cl.
*A41C 3/04* (2006.01)
*A41C 3/12* (2006.01)

(52) U.S. Cl. ........................... 450/37; 450/54; 450/57; 450/81; 2/267; 604/385.07

(58) Field of Classification Search .................. 450/36, 450/37, 54–57, 81; 2/267, 268; 604/385.07; 128/898–891
See application file for complete search history.

(56) References Cited

U.S. PATENT DOCUMENTS

| | | | | |
|---|---|---|---|---|
| 2,891,544 | A * | 6/1959 | London | 604/379 |
| 2,896,623 | A * | 7/1959 | Fitzgerald | 604/385.07 |
| 4,047,534 | A * | 9/1977 | Thomaschefsky et al. | 604/365 |
| 5,092,812 | A * | 3/1992 | Babcock | 450/36 |
| 5,094,647 | A * | 3/1992 | Courtney | 450/36 |
| 5,104,396 | A * | 4/1992 | Oatley et al. | 604/379 |
| 5,297,188 | A * | 3/1994 | Fajac et al. | 378/162 |
| 5,326,305 | A * | 7/1994 | Fochler | 450/57 |
| 5,919,180 | A | 7/1999 | Raimondo | |
| 6,086,247 | A * | 7/2000 | von Hollen | 374/137 |
| 6,264,529 | B1 * | 7/2001 | Logue | 450/36 |
| 6,695,678 | B1 * | 2/2004 | Foley et al. | 450/57 |

* cited by examiner

*Primary Examiner*—Gloria M. Hale
(74) *Attorney, Agent, or Firm*—Sughrue Mion, PLLC

(57) ABSTRACT

Protection disks for breastfeeding mothers, applicable to a mother's breasts ready to give milk, for protecting them and absorbing the flow of milk which comes out spontaneously therefrom, which comprise two kinds of disk clearly differentiated from each other, of which the disks of the first (2) kind having an appreciably different configuration from those of the second (2') and/or are provided with at least one differentiating tactile and/or optical marking (1), in high relief or in low relief, enabling them to be differentiated from other disks of the second kind, intended for applying to the other breast, which are devoid of said marking or having another different marking.

13 Claims, 2 Drawing Sheets

PROTECTION DISKS FOR BREASTFEEDING MOTHERS

This Application is a 371 of PCT/EP2003/014249 filed Dec. 15, 2003; the disclosure of which is incorporated herein by reference.

TECHNICAL FIELD OF THE INVENTION

The invention relates to an improvement in the disks used for protecting the breasts of breastfeeding mothers, whose milk is used for feeding a newborn baby and for absorbing the flow of milk, which spontaneously comes out therefrom.

BACKGROUND OF THE INVENTION

The feeding of a baby is essential for its correct development and for good nutrition it is strongly advised by paediatricians, midwives and other experts in breastfeeding. It is a practice, which contributes many benefits, apart from the nutritional ones, to both mother and child.

Nevertheless, the practice of breastfeeding causes milk leakage after the sucking, as well as pain and hypersensitivity therein.

Different mechanisms exist which adapt to the breasts so as to avoid milk leakage and protect them from knocks and chafing. The embodiment consisting of two disks, one for each breast, is very widespread and is adaptable to the latter and made of absorbent and resistant material.

The same experts also advise, both for the mother and child's benefit, that for each feed, the baby is breastfed with both breasts and starting with the breast last used in the previous feed.

One must bear in mind that caring for a baby requires an effort of both concentration and serenity and that, faced with a series of stimuli and situations such as: hygiene, controlling the feeding schedule, the length of time with each breast, etc., it may be that the person responsible for doing it (the mother), especially if she is starting, needs a period of adaptation and a range of outside resources to make her job easier. In practice, for instance, the fact of having to remember which was the last breast used for feeding the baby, may cause problems to the person responsible for doing it.

Just as different embodiments exist which help in several of the aforementioned aspects, so there continue to be difficulties in other aspects. It is the case of said example, when the mother starts a feed with breast milk, she has to stop to think which breast she ended the previous one with. Having said that, provided that one wants to do it in a way which is most beneficial to both.

EXPLANATION OF THE INVENTION

With the aim of providing a solution to the previously described problems stemming from the lack of resources which help in following the guidelines recommended for the feeding of a newborn baby by breast milk, always giving milk first from the breast with which the previous feed ended, a new protection has been created for the breast at the secretion of milk stage for the feeding of a newborn baby, which at the same time complies with all the technological requirements for permitting all the aforementioned functions.

The protection disks for breastfeeding mothers object of the invention are characterised in that they comprise two kinds of disk clearly differentiated from each other, of which the disks of the first kind have an appreciably different configuration from those of the second and/or are provided with at least one differentiating tactile and/or optical marking, in high relief or in low relief, enabling them to be differentiated from other disks of the second kind, intended for applying to the other breast, which are devoid of said marking or have another different marking.

According to another characteristic of the invention, the differentiating tactile and/or optical marking is removable, so that its application in one of the disks of the second kind convert said disk into one of the first kind.

The protection disks object of the invention are also characterised in that the disks of the first kind and of the second kind can comprise a small deposit, in the form of a bag or inflatable bubble, which constitutes the differentiating marker, capable of being burst or easily deflated.

BRIEF DESCRIPTION OF THE DRAWINGS

Represented in the drawings of this specification is an example of an embodiment of one of the protection disks for breastfeeding applicable to a mother's breast ready to give milk, to protect it and absorb the flow of milk that spontaneously comes out therefrom, object of the present invention. In said drawings.

DETAILED DESCRIPTION OF THE DRAWINGS

The description which follows refers to the above described drawings, which make it possible to appreciate in detail an embodiment example of the protection disks of the present invention.

As can be appreciated in FIGS., 1 to 3, the protection disk represented comprises an optical and tactile marking 1 that makes it possible to distinguish it from other disks that do not have it.

Figure 1:
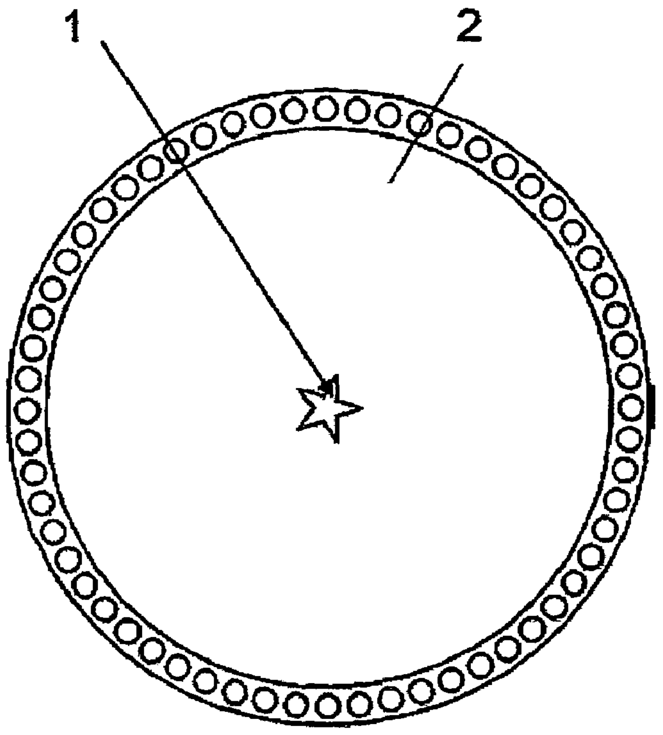
FIG. 1 is a plan view of an embodiment example of the protection disk.
Figure 2:
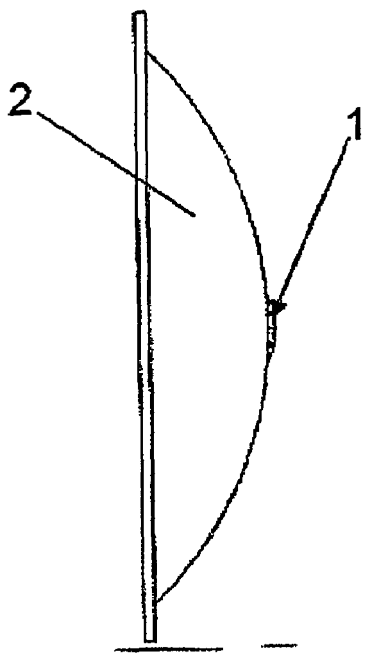
FIG. 2 is a profile view of the disk.
Figure 3:
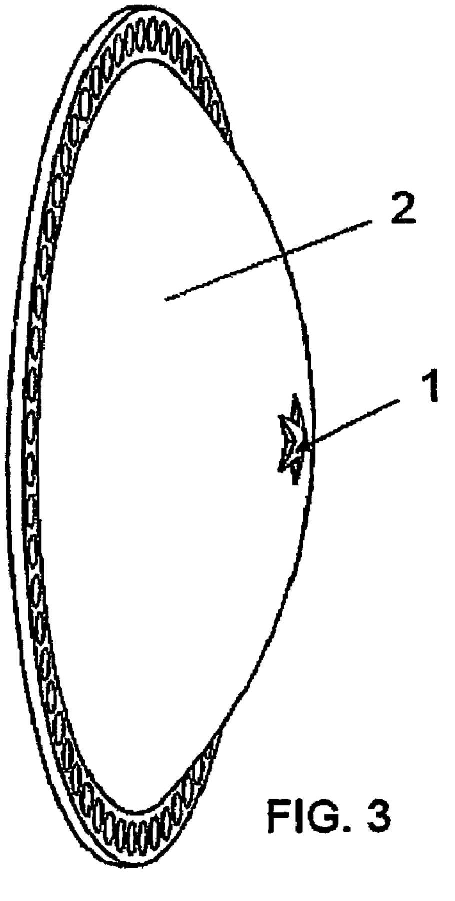
FIG. 3 is a perspective view of the same disk.
Figure 4:
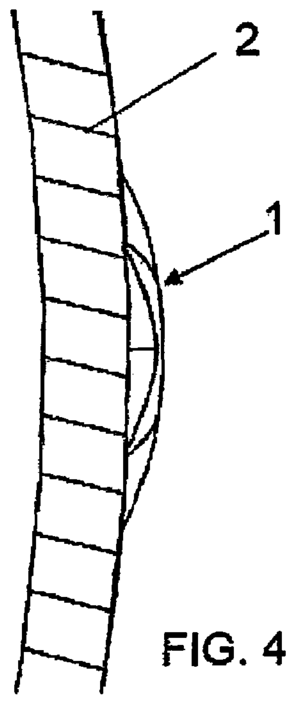
FIG. 4 is a close-up in section of the optical and tactile marking of the embodiment example of the protection disk.

In FIG. 4 we can observe an example of the thickness of the protection disk as regards the marking in low or high relief, so that the latter is small in order not to show on the clothing superimposed on it and at the same time being enough to be noticeable by touch.

The protection disks object of the present invention consist of an improvement on the absorbent disks currently existing on the market, adaptable to breasts which are at the breast milk secretion stage.

In accordance with FIGS. 1 to 5, the protection disks comprise two kinds of disks 2-2', clearly differentiated from each other. The disks are differentiated from each other because the disks of the first kind 2 are of a different configuration from the first kind 2'. Obviously, the different configuration of the disks 2-2' in themselves constitute an optical and tactile differentiating marking. In any case, the disks can also be differentiated from each other because the disk in the first kind 2 is provided with a differentiating optical and/or tactile marking 1, in high relief or in low relief, whereas the disk of the second kind 2' similar to this one, placed on the other breast, lacks said marking 1 or has another different marking 1'. Arranged on the breasts with differentiating markings and at the same time protecting and absorbing the flow of milk spontaneously coming out of them, helps the mother to identify the breast with which to start the next feed for the baby.

The differentiating marking 1-1' is situated in a noticeable area of the corresponding kind 2-2' to differentiate, so that visually and/or by touch, whether in a lit up or dark place, it is possible to recognize the breast with which to start the feed at that time. The marking 1-1' can be of high relief or low relief with a determined shape, but it has to be discrete in such a way that it does not show through clothing and have an non-aesthetic effect. Said marking 1-1' can be just the one or they can be several, different and/or repetitive, for example a disk of one colour/shape/feel and the other of another colour/shape/feel.

The marking 1-1' can be incorporated into the product (printed, engraved, patterned, etc.) in the production process or constitute a removable accessory which, by means of an adhesive or similar system, the consumer uses at the time of use, fixing it to the disk that she wants to differentiate.

Figure 6:
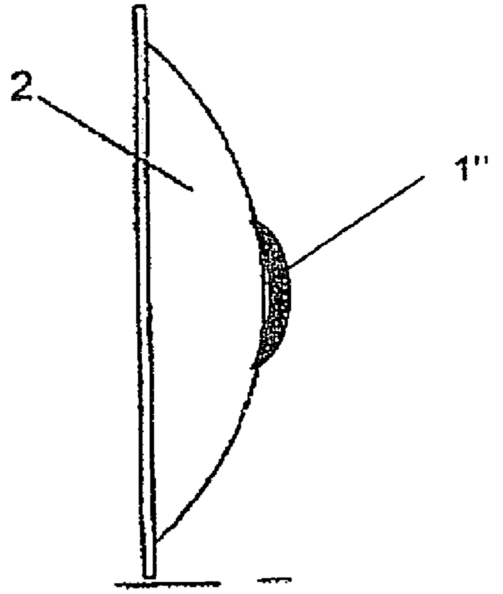
FIG. 6 schematically illustrates an exemplary embodiment of the present invention in which a bubble is the differentiating marker.

Also provided for is the possibility of both disks 2-2' being the same and that those that have to be differentiated comprise a small deposit, in the form of a bag or inflatable bubble, for example, bubble 1" in FIG. 6, full of a fluid or plastically deformable material, designed so that the user may with relative ease at the time of use, burst, deflate, or press, the aforementioned deposit of one of the disks being permanently deformed, thus differentiating which is the next breast to start with in the next feed.

Figure 5:
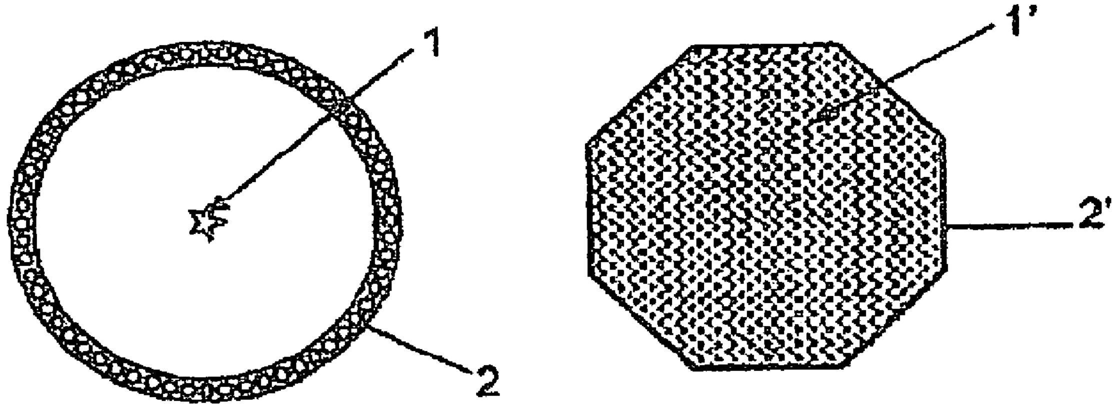
FIG. 5 consists of a plan view of another form of embodiment of the invention.

In accordance with FIG. 5, the protection disks comprise a first kind 2 of disks with an appreciably rounded configuration; and a second kind 2' of disk with an appreciably hexagonal configuration. Obviously, the configuration of the disks 2-2' may consist of any other geometric shape. In the case represented it is also envisaged that the two kinds 2-2' of disks can also be differentiated by a differentiating tactile and/or optical marking 1-1' which consists of providing the disks of the first kind 2 with a smooth surface, and the disks of the second kind 2' with a rough surface.

If one makes use of the protective disks of the present invention with two kinds 2-2' of disks clearly differentiated from each other by their different configuration and/or by an optical and/or tactile marking 1-1', the first disk 2 can be applied to the breast that has been used last to feed the baby and the second 2' for the other, or vice-versa, but obviously one will have to keep the criteria for identifying the breast and avoid confusion. Therefore, the next time a feed is started, just by looking at or touching the protective disks one will immediately know which breast to start with. In addition, for this it may be a good idea for the marking to be a meaningful icon for the person using it; a drop of milk, lips, an "OK", a star, etc.

The invention claimed is:

1. A system of absorbent breast feeding protection disks for selective application to alternate breasts in connection with breast feeding, the system comprising:

at least two types of alternative breast feeding disks each having an outer surface and an inner surface, each type of disk differentiated from the other by a user of the system based on a recognizable configuration on the outer surface of the disk selected from one of a low relief tactile marking one of a high relief tactile marking and one of an optical marking that is within a periphery of the outer surface of the disk; and wherein each disk is configured as an absorbent protective disk comprising an absorbent material and for placement in a bra cup to absorb spontaneous flow of milk from a breast.

2. The system according to claim 1 characterised in that the differentiating recognizable configuration is removable by the user, so that application of the recognizable configuration to or removal of the recognizable configuration from a disk outer surface of one type converts that disk into the disk of the other type.

3. The system according to claim 1 characterised in that the disks of one type comprises on an outer surface of the disk an air bubble that can be converted into the disk of the other type by deflating or bursting the air bubble.

4. An absorbent breastfeeding protection kit for a breastfeeding mother, the kit comprising a pair of protective disks, the disks comprising:

a first disk comprising an absorbent material and configured to be placed between one of the breastfeeding mother's breast, which is a first breast, and a cup of a bra or other garment worn there over, so as to directly absorb the flow of milk that comes out from the first breast; and a second disk comprising an absorbent material and configured to be placed between the other one of the breastfeeding mother's breasts, which is a second breast, and another cup of a bra or other garment worn there over, so as to directly absorb the flow of milk that comes out from the second breast, thereby protecting the cup of the bra or other garment worn there over; and wherein the first disk is noticeably distinguishable to the breastfeeding mother from the second disk due to one or more of the following:

(a) the first disk having, on an outer surface of the disk and within a periphery of the outer surface of the disk an observable design that is not present on the second disk, (b) the first disk having a tactile marking on the outer surface of the disk, in high relief or in low relief, not present in the second disk, (c) the first disk having an optical marking on the outer surface of the disk and within the periphery of the outer surface of the disk that is not present in the second disk; and (d) the first disk having an observable shape that is different from an observable shape of the second disk; and wherein the distinguishable disks are configured to be used by the breastfeeding mother to identify a breast with which to start the next breastfeeding; and wherein the first disk and the second disk do not provide lift support for the breastfeeding mother's breasts.

5. The kit according to claim 4, wherein the first disk is noticeably distinguishable to the breastfeeding mother from the second disk due to the first disk having, on the outer surface of the disk and within a periphery of the outer surface of the disk a visible design that is not present on the second disk.

6. The kit according to claim 4, wherein the first disk is noticeably distinguishable to the breastfeeding mother from the second disk due to the first disk having a tactile marking on the outer surface of the disk, in high relief or in low relief, not present in the second disk.

7. The kit according to claim 6, wherein the tactile marking is a bubble configured to be burst by the breastfeeding mother and, once burst, resembles the second disk.

8. The kit according to claim 6, wherein the tactile marking is a bubble configured to be deformed by the breastfeeding mother and, once deformed, resembles the second disk.

9. The kit according to claim 4, wherein the first disk is noticeably distinguishable to the breastfeeding mother from the second disk due to the first disk having an optical marking on the outer surface of the disk and within the periphery of the outer surface of the disk that is not present in the second disk.

10. A protection device system for a breastfeeding mother, comprising a pair of disks comprising absorbent material and configured to be placed between one of the breastfeeding mother's breast and a cup of a bra or other garment so as to directly absorb the flow of milk that comes out from the first breast, each disk on an outer surface thereof comprising an outwardly visible and tactile marker in high relief that is a bubble configured to be deflated by the breastfeeding mother, thereby deforming the marker; and wherein the pair of disks do not provide lift support for the breastfeeding mother's breasts.

11. The kit according to claim 4, wherein the first disk is noticeably distinguishable to the breastfeeding mother from the second disk due to the first disk having having an observable shape that is different from an observable shape of the second disk.

12. A method of breastfeeding, comprising:

providing an absorbent breastfeeding disk system of at least two types of alternative absorbent breast feeding disks each having an outer surface and an inner surface, each type of disk differentiated from the other by a user of the system based on a recognizable and visible or tactile structure;

breastfeeding a child; and applying one type of disk of the two disk types to one breast under a wearer's garment and another type of disk to the other breast under a wearer's garment so as to uniquely mark the breast last used for breastfeeding.

13. The method according to claim 12, wherein the recognizable structure is on the outer surface of the disk and is one of a low relief tactile marking, one of a high relief tactile marking, one of an optical marking, and one of a shaped structure; and wherein each disk is configured as an absorbent protective disk comprising an absorbent material and for placement in a bra cup to absorb spontaneous flow of milk from a breast.

* * * * *